US00PP11267P

United States Patent [19]

Churchus

[11] Patent Number: Plant 11,267

[45] Date of Patent: Mar. 7, 2000

[54] DOUBLE IMPATIENS PLANT NAMED 'GOLDEN SURPRISE'

[76] Inventor: John William Churchus, 4 Fiona Drive, Devon Meadows, Victoria 3977, Australia

[21] Appl. No.: 08/963,517

[22] Filed: Nov. 3, 1997

[51] Int. Cl.[7] ..... A01H 5/00

[52] U.S. Cl. ..... Plt./317

[58] Field of Search ..... Plt./87.6, 319, Plt./317

*Primary Examiner*—Howard J. Locker
*Assistant Examiner*—Anne Marie Grünberg
*Attorney, Agent, or Firm*—C. A. Whealy

[57] ABSTRACT

A new and distinct cultivar of Double Impatiens plant named 'Golden Surprise', characterized by its unique and stable light green to light yellow and green variegated foliage; light purple to white and bright purple bi-colored flowers; consistently double and symmetrical flower form; numerous flowers per plant; freely branching, dense and bushy plant habit; low-growing, outwardly spreading to cascading, and mounded plant habit; suitable for hanging baskets and patio containers; and excellent landscape performance.

1 Drawing Sheet

The present invention relates to a new and distinct cultivar of Double Impatiens plant, botanically known as *Impatiens walleriana*, and hereinafter referred to by the cultivar name Golden Surprise.

The new cultivar is a spontaneous branch mutation of the *Impatiens walleriana* cultivar Blueberry Swirl (not patented). The new cultivar was discovered and selected by the inventor in a controlled environment in Devon Meadows, Victoria, Australia in 1991, as a mutation of the more vigorous and solid green leaf-colored cultivar Blueberry Swirl. Asexual reproduction of the new cultivar by terminal cuttings taken at Devon Meadows, Victoria, Australia, has shown that the unique features of this new Double Impatiens are stable and reproduced true to type in successive generations of asexual reproduction.

The following traits have been repeatedly observed and are determined to be the unique characteristics of 'Golden Surprise'. These characteristics in combination distinguish the new Double Impatiens as a new and distinct cultivar:

1. Unique and stable light green to light yellow and green variegated foliage.
2. Unique light purple to white and bright purple bi-colored flowers.
3. Consistently double and symmetrical flower form. 4. Numerous flowers per plant.
5. Freely branching, dense and bushy plant habit.
6. Low-growing, outwardly spreading to cascading, and mounded plant habit, suitable for hanging baskets and patio containers.
7. Excellent landscape performance.

The new Double Impatiens has not been observed under all possible environmental conditions. The phenotype may vary significantly with variations in environment such as temperature and light level, without, however, any variance in genotype.

BRIEF DESCRIPTION OF THE PHOTOGRAPHS

The accompanying colored photographs illustrate the overall appearance and flower color of the new Double Impatiens, showing the colors as true as it is reasonably possible to obtain in colored reproductions of this type.

The photograph at the top of the sheet comprises a top perspective view of a typical plant of the Double Impatiens.

The photograph at the bottom of the sheet comprises a close-up view of typical leaves and flowers of the new Double Impatiens. Flower and foliage colors in the photographs may appear different from the actual colors due to light reflectance.

DETAILED BOTANICAL DESCRIPTION

The following observations, measurements, values, and comparisons describe plants grown under outdoor production conditions in 16.5-cm containers in Keller, Tex., in full and partial shade during the summer.

In the following description, color references are made to The Royal Horticultural Society Colour Chart except where general terms of ordinary dictionary significance are used.

Botanical classification: *Impatiens walleriana* cultivar Golden Surprise.

Parentage: Spontaneous branch mutation of *Impatiens walleriana* cultivar Blueberry Swirl (not patented).

Propagation:

- *Type cutting.*—Terminal cuttings.
- *Time to initiate roots.*—Summer: About 7 days at a temperature of 15° C. Winter: About 14 days at a temperature of 10° C.
- *Rooting habit.*—Numerous, strong, fine, and freely-branching.

Plant description:

- *Form.*—Low-growing, outwardly spreading to cascading, and mounded plant habit. Freely branching, dense and bushy growth. Flowers face upright or outward.
- *Usage.*—Suitable for 10 to 25-cm containers; recommended for hanging baskets and patio containers; excellent garden performance.
- *Vigor.*—Moderate and moderate growth rate.
- *Plant height.*—About 10 cm.
- *Plant spread.*—About 50 cm.
- *Branching habit.*—Freely branching with numerous lateral branches, branches very strong and flexible.
- *Lateral branches.*—Length: About 19 cm. Diameter: About 8 mm. Internode length: About 1.7 cm. Color: Translucent, light green, close to 144C, with numerous red-purple, 59A, spots and streaks.
- *Foliage description.*—Leaves simple, generally symmetrical, abundant, alternate, and flat in aspect. Length: About 4 cm. Width: About 3.2 cm. Shape:

Broadly ovate with acuminate apex, cuneate base and crenate margin. Texture: Smooth. Color: Light green to light yellow and green variegated leaves; green at center with light green/light yellow at margin. Actual shape and size of yellow and green areas is variable. Young leaves, upper surface: Yellow areas: 11C to light green, 146C. Green areas: 146A/144A. Young leaves, lower surface: Yellow areas: 10C to light green. Green areas: Close to 146A/146B with red (dulled 178A) spots/blotches. Fully expanded leaves, upper surface: Yellow areas: 10C/10D/11B/11C/11D. Green areas: Close to 147A/147B and lighter green areas, 147C. Fully expanded leaves, lower surface: Yellow areas: 11B/11C/11D to light green. Green areas: Close to 147B with red (dulled 178A) spots/blotches. Venation, upper surface: Similar to leaf surface color, 146A/147A/147B, iridescent. Venation, lower surface: 146A. Petiole: Length: About 2.75 cm. Diameter: About 2 mm. Color: Very light green to white.

Flower description:

*Flower type and habit.*—Light purple to white and bright purple bi-colored flowers, very iridescent. Consistently double and symmetrical flowers. Freely and continuously flowering. Flower buds open similar to a rose in fullness. Flowers arise from leaf axils, terminal bud opening first. Usually three or four flowers per lateral branch. Flowers face upright or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 2 cm.

*Flower buds.*—Length: About 1.2 cm. Diameter: About 9 mm. Shape: Ovoid. Color: Purple, 64A, and light pink, 65D.

*Petals/petaloids.*—Quantity: Numerous, typically more than 15. Length: About 1.75 cm. Width: About 1.4 cm. Shape: Obovate with rounded apex, cuneate base and entire margin. Texture: Satiny, smooth. Color: Light purple to white and bright purple bi-colored. Actual shape and size of light purple to white and bright purple areas is variable. Center and base of petals are typically purple; white areas are typically located at apex and margins. When opening, upper surface: Very iridescent, light purple, 75A/75B/75C, to white, and bright purple, 67A. When opening, lower surface: Very iridescent, light purple, 75A/75B/75C, to white, and bright purple, 67A. Mature, upper surface: Very iridescent, light purple, 75A/75B/75C, to white, and bright purple, 67A. Mature, lower surface: Very iridescent, light purple, 75A/75B/75C, to white, and bright purple, 67B.

*Spur.*—Length: About 2.5 cm. Shape: Narrow and curved. Color: Initially green, close to 144A, becoming light purple, close to 75C.

*Peduncles.*—Length: About 2.25 cm. Angle: Upright to outwardly arching. Strength: Moderate, flexible. Color: Glossy, translucent, light green.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance to pathogens has not been observed.

It is claimed:

1. A new and distinct Double Impatiens plant named 'Golden Surprise', as illustrated and described.

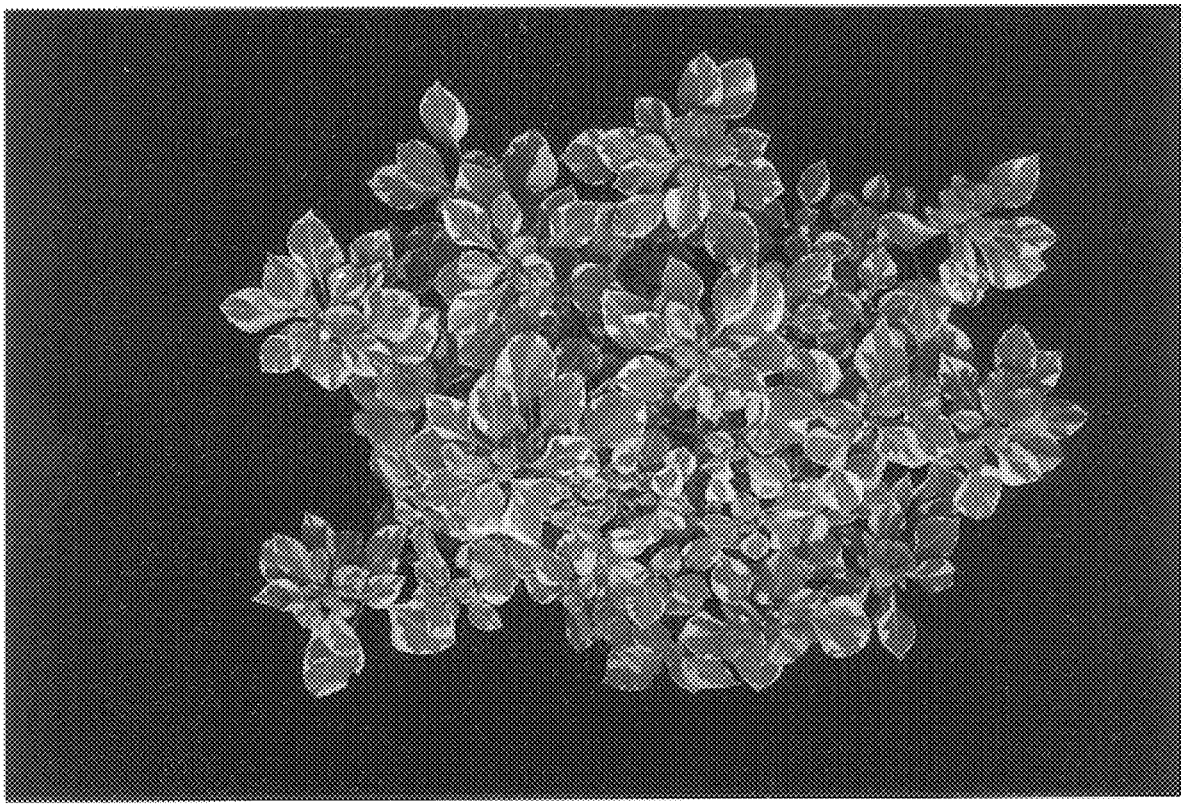
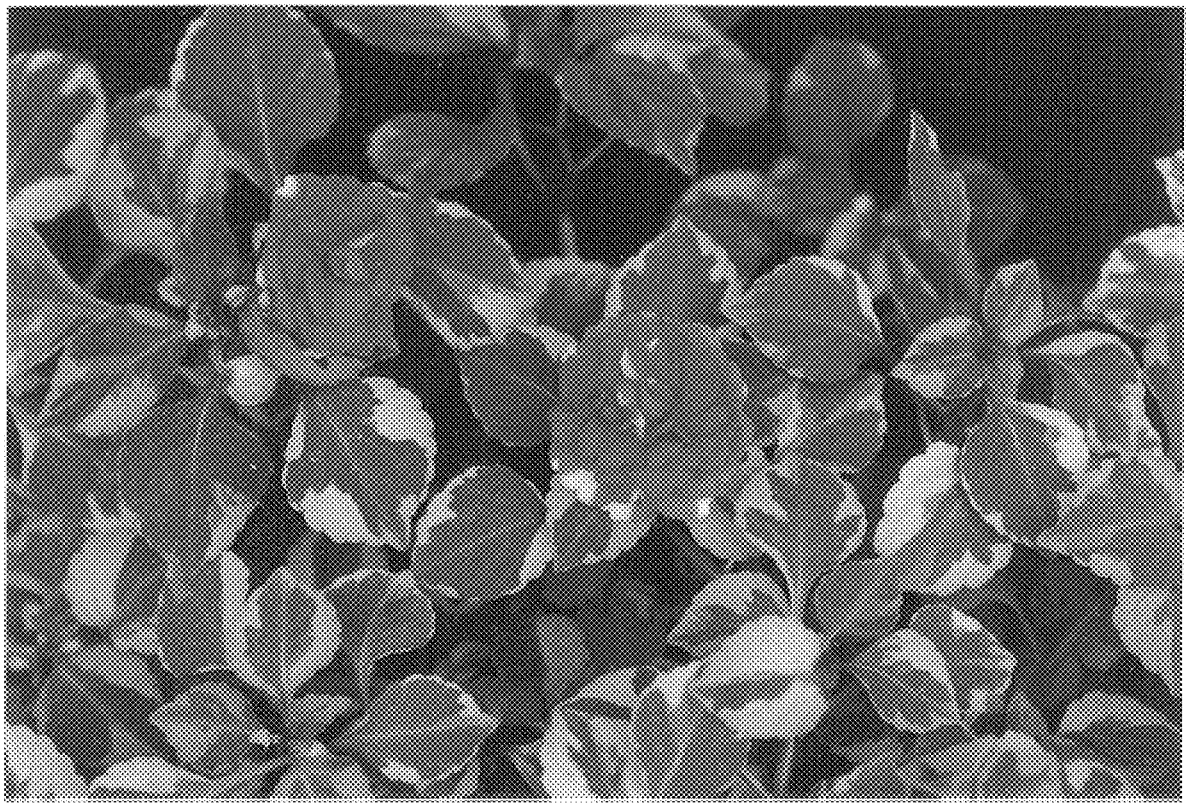

* * * * *